United States Patent [19]
Kofod et al.

[11] Patent Number: 6,140,096
[45] Date of Patent: Oct. 31, 2000

[54] ENZYME WITH ENDO-1,3(4)-β-GLUCANASE ACTIVITY

[75] Inventors: Lene Venke Kofod, Uggerløse; Lene Nonboe Andersen, Allerød; Markus Sakari Kauppinen, København N; Stephan Christgau, Gentotte; Henrlk Dalbøge, Virum; Hans Sejr Olsen, Holts; Jens Breinholt, Bagsværd, all of Denmark

[73] Assignee: Novo Nordisk A/S, Bagsvaerd, Denmark

[21] Appl. No.: 09/098,580

[22] Filed: Jun. 17, 1998

Related U.S. Application Data

[62] Division of application No. 08/737,526, filed as application No. PCT/DK95/00188, May 11, 1995.

[30] Foreign Application Priority Data

May 11, 1994 [DK] Denmark .................................. 546/94

[51] Int. Cl.[7] ................................ C12N 9/24; C12N 1/15; C12N 1/19; C12N 9/36; C12N 5/00; C07H 21/04
[52] U.S. Cl. ........................ 435/200; 435/209; 435/254.1; 435/254.11; 435/254.21; 435/254.3; 435/325; 435/410; 536/23.2
[58] Field of Search ...................... 435/200, 209, 435/254.1, 254.11, 254.21, 254.3, 325, 410; 536/23.2

[56] References Cited

FOREIGN PATENT DOCUMENTS

WO 93/20193  10/1993  WIPO .
WO 94/07998   4/1994  WIPO .

OTHER PUBLICATIONS

S.M. Pitson et al., "Noncellulolytic Fungal β–Glucanases: Their Physiology And Regulation", Enzyme Microb. Technol., 1993, vol. 15, Mar. 1993, pp. 178–192.

*Primary Examiner*—Elizabeth Slobodyansky
*Attorney, Agent, or Firm*—Steve T. Zelson; Valete A Gregg

[57] ABSTRACT

An enzyme having endo-1,3(4)-β-glucanase activity is described which is encoded by the DNA sequence ATGTGGTCTCCCAAGGTTGCTGCTGCCGTCCTCGCCTTTGTTGGTGCTACCAACGCCTGGCAGCCCCCGACCTACAGCGGCTTCAACTTGGTCTGGACTGACACCTTCGCTGGCAACGGTGGCACTTCTCCTA ACCAGAACAACTGGAACATCATCACCGGAAACTTGAACGTCAACGCCGAGCAGGAGACCTACTCCTCCAGCACC GCCAATGTTCAGCTCAGTGGTGGCAGCACCCTTCAGCTGGTCCCCTGGAGAGACAGCAGCAAGGGAACCAGCAC CTTTGGTGGCTGGACCTCCGGTCGTCTTGAGTCCAAGTACACATTCACTCCCGCGGCCGGCAAGGTCACCCGTCTTGAAGCCGCCATCCGCTTCGGCAGCAACGCTCAGGCCAACAAGCAGGGTATCTGGCCTGCTTTCTGGATGCTGGGT GACTCCCTCCGTCAACCGGGCGGCAGCTGGCCCAACTGTGGTGAGATCGACATCATGGAGACTGTCGACGGCCAGGCTACCGGCCACGGTACCCTTCACTGCGACGTCTACCCCGGCGGTATCTGCAACGAGGGTAACGGTATTGGAGG CCCTGTCAACATCGCCAACGTCAACGACTGGCACGCTTGGCGTGTTGAGATCGACCGCACTCCCAGCAGCTGGCAATCCGAGACCCTCACCTGGTCCCTCGACGGCACCATCTACTTCCAGATCACTGGCTCTCGCATTGGCAACCAGGG CGTCTGGAACAACATTGCTCACAGCCCCCTCTTCTTCATTCTTAACGTTGCTGTCGGTGGCAACTGGCCTGGCAAC CCCAACAGCGCTACCCTCGATGGCTACGGAAGCATGATGGAGGTTGGCTACGTCGCTCAGTACTCTACCTAA (SEQ ID NO:3).

22 Claims, 6 Drawing Sheets

ENZYME WITH ENDO-1,3(4)-β-GLUCANASE ACTIVITY

CROSS-REFERENCE TO RELATED APPLICATIONS

This application is a divisional of application Ser. No. 08/737,526 filed on Nov. 8, 1996, now U.S. Pat. No. 5,871,966 which is a 871 of PCT/DK95/00188 filed on May 11, 1995 and claims priority under 35 U.S.C. 119 of Danish application Ser. No. 546/94 filed May 11, 1994, the contents of which are fully incorporated herein by reference.

FIELD OF INVENTION

The present invention relates to an enzyme with endo-1,3(4)-β-glucanase activity, a DNA construct encoding the enzyme, a method of producing the enzyme, an enzyme preparation containing the enzyme, the use of said enzyme or said enzyme preparation for a number of uses including the degradation or modification of β-glucan containing materials.

Also contemplated is an isolated substantially pure culture of Saccharomyces cerevisiae NN049006, transformed with a DNA sequence derived from Acremonium sp. (CBS 265.95).

BACKGROUND OF THE INVENTION

Endo-1,3(4)-β-glucanases (E.C. no. 3.2.1.6) constitute a group of hydrolases, which catalyse endo hydrolysis of 1,3-β-D-glycosidic linkages in β-1,3-glucans, such as curdlan, lichenan and laminarin, a major component of the cell walls of fungal (including yeast) cells, and β-1,4 bonds in mixed β-1,3-1,4-glucans such as cereal β-D-glucans. The authorized systematic name is 1,3-(1,3;1,4)-β-D-glucan 3(4)-glucanohydrolase, and the common name is Laminarinase, but the abbreviated term endo-1,3(4)-β-glucanase is used in the present specification.

Cell walls of fungal microorganisms such as yeasts and fungi are complex structures which, in addition to β-glucan, comprise a number of other components. For instance, yeast cell walls comprise a protein-mannan complex layer in addition to a glucan layer (Andrews and Asenjo, 1987), and cell walls of filamentous fungi additionally comprise varying amounts of chitin and chitosan (cf. Hudson, H. J., 1986).

It is well-known that microorganisms produce a number of valuable products such as colorants, flavourants, vitamins, the isolation of which is desirable. The isolation of intracellularly produced products requires that the cell walls of the microbial producers be ruptured or lysed.

Because of the complex composition of microbial cell walls, the rupture or lysis of cell walls has traditionally been carried out by rather vigorous treatments involving the use of strong chemicals and/or mechanical means.

Enzymatic lysis and disruption of microbial cells have been suggested as a desirable alternative to chemical or mechanical rupture in the production of yeast extracts or other intracellulary produced products (Andrew and Asenjo (1987); Phaff (1977)). Furthermore, enzymatic lysis has been suggested for use in the preparation of protoplast from fungi or yeasts (Hamlyn et al., 1981). A number of commercially available enzyme preparations useful in the enzymatic lysis of yeast and fungal cells are available. Such products normally comprise multiple enzymatic activities, e.g. including β-1,3- and/or β1,6-glucanase, protease, chitinase, mannanase and other enzymes capable of cleaving cell wall components.

According to Pitson et al., (1993), filamentous fungi such as Rhizopus arrhizus, Trichoderma longibranchiatum and Penicillum funiculosium are known to produce enzymes exhibiting endo-1,3(4)-β-glucanase activity.

The object of the invention is to provide a novel endo-β-glucanase and a method for producing the endo-β-glucanase in a better yield and higher purity than hitherto possible, as well as the use of the endo-1,3(4)-β-glucanase either alone or in combination with other enzymes for the degradation of plant or microbial cell wall tissue. Also it is the object of the invention to provide novel products, wherein the proportion of the endo-1,3(4)-β-glucanase is increased relative to the proportion of the original product.

It would be desirable to be able to improve the cell wall degrading or modifying capability of such enzyme preparations and further to be able to more specifically control the degradation or modification of specific plant or microbial cell wall components.

SUMMARY OF THE INVENTION

The present inventors have now surprisingly succeeded in isolating and characterizing a DNA sequence which encodes an enzyme exhibiting endo-1,3(4)-β-glucanase activity, thereby making it possible to prepare single-component endo-1,3(4)-β-glucanases.

Accordingly, in a first aspect the invention relates to a DNA construct comprising a DNA sequence encoding an enzyme exhibiting endo-β-glucanase activity, which DNA sequence
a) comprises the DNA sequence shown in SEQ ID No. 3, or
b) comprises an analogue of the DNA sequence shown in SEQ ID No. 3, which
  i) is homologous with the DNA sequences shown in or SEQ ID no. 3, and/or
  ii) hybridizes with the same oligonucleotide probe as the DNA sequence shown in SEQ ID no. 3, and/or
  iii) encodes a polypeptide which is homologous with the polypeptide encoded by a DNA sequence comprising the DNA sequence shown in SEQ ID No. 3, and/or
  iv) encodes a polypeptide which is immunologically reactive with an antibody raised against a purified endo-1,3(4)-β-glucanase encoded by the sequence shown in SEQ ID No. 4 derived from Trichoderma harzianum, CBS 243.71.

In a specific embodiment of the invention the above mentioned DNA sequence encoding an enzyme exhibiting endo-1,3(4)-β-glucanase activity.

In the present context, the "analogue" of the DNA sequence shown in SEQ ID No. 3 is intended to indicate any DNA sequence encoding an enzyme exhibiting endo-β-glucanase activity (such as endo-1,3-β-glucanase and endo-1,3 (4)-β-glucanase), which has the properties i)–iv) above. Typically, the analogous DNA sequence
  is isolated from another or related (e.g. the same) organism known or contemplated to produce the enzyme with endo-β-glucanase activity on the basis of the DNA sequence shown in SEQ ID No. 3 or any of the DNA sequences shown in SEQ ID Nos. 1 or 2, e.g. using the procedures described herein, or
  is constructed on the basis of the DNA sequence shown in SEQ ID No. 3 or any of the DNA sequences shown in SEQ ID Nos. 1 or 2, e.g. by introduction of nucleotide substitutions which do not give rise to another amino acid sequence of the endo-β-glucanase encoded by the DNA sequence, but which correspond to the codon usage of the host organism intended for production of the enzyme, or by introduction of nucleotide substitutions which do give rise to a different amino acid sequence and therefore, possibly, a different protein structure which might give rise to an endo-β-glucanase mutant with different properties than the native enzyme. Other examples of possible modifications are insertion of one or more nucleotides into the sequence, addition of one or more nucleotides at either end of the sequence, such as a cellulose binding domain, or deletion of one or more nucleotides at either end or within the sequence. For instance, the analogous DNA sequence may be a subsequence of the DNA sequence shown in SEQ ID No. 3 or sequences SEQ ID No. 1 or 2.

It will be understood that DNA sequences or parts of the DNA sequences shown in SEQ ID Nos. 1 and SEQ ID No. 2 are sequences which may be used for isolating the entire DNA sequence encoding the enzyme with endo-β-glucanase activity. The term "analogue" is intended to include said entire DNA sequence shown in SEQ ID NO. 3, which comprises at least a part of the sequences shown in SEQ ID Nos. 1 or 2 or parts thereof.

The hybridization referred to in i) above is intended to indicate that the analogous DNA sequence hybridizes to the same probe as the DNA sequence encoding the endo-1,3 (4)-β-glucanase enzyme under certain specified conditions which are described in detail in the Materials and Methods section hereinafter. Normally, the analogous DNA sequence is highly homologous to the DNA sequence such as at least 40% to 50% homologous, better at least 60% to 70% homologous to any of the sequences shown above encoding an endo-β-glucanase of the invention, such as at least 75%, at least 80%, at least 85%, at least 90% or even at least 95% homologous to any of the sequences shown above.

The degree of homology referred to in i) above is determined as the degree of identity between the two sequences indicating a derivation of the first sequence from the second. The homology may suitably be determined by means of computer programs known in the art. Typically, the DNA sequence exhibits a degree of identity of at least 40% to 50%, better at least 60% to 70%, such as at least 80% or 90% with the DNA construct comprising the DNA sequence shown in SEQ ID No. 3, or at least a part of the DNA sequence shown in SEQ ID No. 1 and/or 2.

The degree of homology referred to in iii) above is determined as the degree of identity between the two sequences indicating a derivation of the first sequence from the second. The homology may suitably be determined by means of computer programs known in the art. Typically, the polypeptide encoded by an analogous DNA sequence exhibits a degree of homology of at least 40% to 50%, better at least 60% to 70%, such as at least 80% or 90% with the enzyme encoded by a DNA construct comprising the DNA sequence shown in SEQ ID No. 3, or any of the partial DNA sequence SEQ ID No. 1 and/or 2.

The term "derived from" in connection with property iii) above is intended not only to indicate an endo-1,3(4)-β-glucanase produced by strain CBS 243.71, but also an endo-1,3(4)-β-glucanase encoded by a DNA sequence isolated from strain CBS 243.71 and produced in a host organism transformed with said DNA sequence. The immunological reactivity may be determined by the method described in the Materials and Methods section below.

In further aspects the invention relates to an expression vector harbouring a DNA construct of the invention, a cell comprising the DNA construct or expression vector and a method of producing an enzyme exhibiting endo-1,3(4)-β-glucanase activity which method comprises culturing said cell under conditions permitting the production of the enzyme, and recovering the enzyme from the culture.

In a still further aspect the invention relates to an enzyme exhibiting endo-β-glucanase activity, which enzyme
a) is encoded by a DNA construct of the invention, and/or
b) produced by the method of the invention, and/or
c) is immunologically reactive with an antibody raised against a purified endo-1,3(4)-β-glucanase shown in SEQ ID No. 4 derived from Trichoderma harzianum, CBS 243.71.

Said isolated enzyme of the invention has been characterized as described in the examples below. For instance it was found that the apparent molecular weight ($M_w$), determined by SDS-PAGE is about 31 kDa. Further the apparent pI (isoelectric point) was found to be about 5,1.

Also kinetic parameters and the specific activity were determined. The specific activity of the endo-1,3(4)-β-glucanase at 30° C., pH 5.0 was around 100–200 U/mg enzyme and Km was around 0.02 to 0.06% β-1,3-1,4-glucan.

Figure 1:
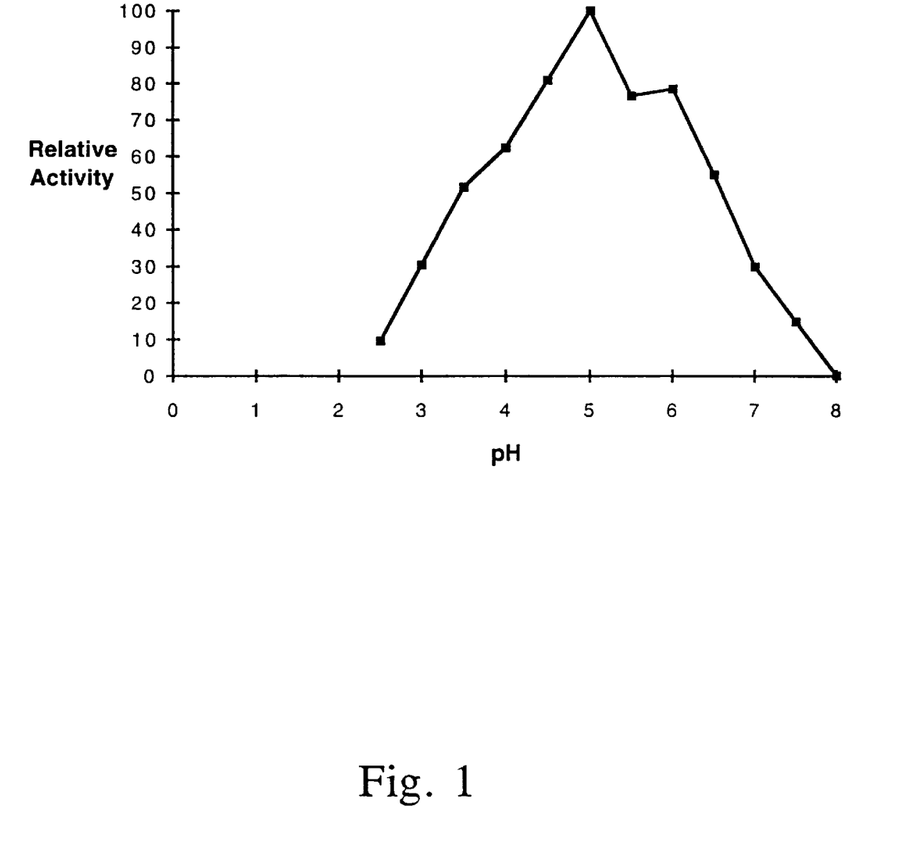
FIG. 1 shows the activity of the endo-β-1,3(4)-glucanase of the invention as a function of pH at 30° C.

Further, it was seen that the endo-1,3(4)-β-glucanase of the invention has more than 60% activity between pH 4.0 and 6.5 and optimal activity at pH 4.5–5.5 (see FIG. 1). The enzyme activity was found to be optimal at 50° C. (see FIG. 2).

Furthermore it was verified by depolymerization of β-glucans and by $^{13}C$ NMR characterization that the isolated enzyme exhibits endo-1,3(4)-β-glucanase activity, it is described in example 9 and 10.

In a still further aspect, the present invention relates to an enzyme preparation useful for a number of purposes including the degradation or modification of β-glucan containing materials, in particular microbial cell wall material, and/or useful for degradation or modification of plant cell wall components, said preparation being enriched with an enzyme exhibiting endo-1,3(4)-β-glucanase activity as described above. In final aspects the invention relates to the use of the enzyme of the invention or an enzyme preparation of the invention for various purposes in which degradation or modification of plant or microbial cell wall containing material is desirable.

DETAILED DESCRIPTION OF THE INVENTION

The DNA sequence of the invention encoding an enzyme exhibiting endo-β-glucanase activity may be isolated by a general method involving
  cloning, in suitable vectors, a DNA library from Trichoderma harzianum,
  transforming suitable yeast host cells with said vectors,
  culturing the host cells under suitable cond itions to express any enzyme of interest encoded by a clone in the DNA library, screening for positive clones by determining any endo-β-glucanase activity of the enzyme produced by such clones, and isolating the enzyme encoding DNA from such clones.

The general method is further disclosed in WO 93/11249 which is hereby incorporated by reference. A more detailed description of the screening method is given in Example 1 below.

The DNA sequence coding for the enzyme may for instance be isolated by screening a cDNA library of *Trichoderma harzianum*, e.g strain CBS 243.71, publicly available from the Centraalbureau voor Schimmelcultures, Delft, NL, and selecting for clones expressing the appropriate enzyme activity (i.e. endo-1,3(4)-β-glucanase activity as defined by the ability of the enzyme to hydrolyse β-1,3(4)-glucan bonds of a suitable substrate such as AZCL-curdlan and AZCL-glucan, cf. the Materials and Methods section hereinafter). The appropriate DNA sequence may then be isolated from the clone by standard procedures, e.g. as described in Example 1.

It is expected that a DNA sequence coding for a homologous enzyme, i.e. an analogous DNA sequence, is obtainable from other microorganisms. For instance, the DNA sequence may be derived by similarly screening a cDNA library of another microorganism, in particular a fungus, such as a strain of an Aspergillus sp., in particular a strain of *A. aculeatus* or *A. niger*, a strain of another Trichoderma sp., in particular a strain of *T. reesie, T. viride, T. longibrachiatum* or *T. koningii* or a strain of a Fusarium sp., in particular a strain of *F. oxysporum*, or a strain of a Humicola sp., a strain of Rhizopus sp., in particular *Rhizopus arrhizus*, or a strain of an Acremonium sp., or a strain of a Botrytis sp., or a strain of Penicillium sp. or and strain of a Scleotium sp.

A specific example of a such DNA sequence encoding a homologous enzyme can be derived from Acremonium sp. (CBS 265.95). Two partial sequences of the entire DNA sequence encoding a such enzyme are shown in SEQ ID No. 5 and SEQ ID No. 6.

An isolate of a *Saccharomyces cerevisiae* transformed with the expression plasmid PYES 2.0 (Invitrogen), comprising the cDNA sequences, shown in SEQ ID No. 5 and SEQ ID No. 6, has been deposited with the Deutsche Sammlung von Mikroorganismen und Zellkulturen GmbH, Mascheroder Weg 1b, D-3300 Braunschweig, Federal Republic of Germany, (DSM), for the purposes of patent procedure on the date indicated below. DSM being an international depository under the Budapest Treaty affords permanence of the deposit in accordance with rule 9 of said treaty.

Deposit date: 11.05.95
Depositor's ref.: NN049006
DSM designation: DSM 9970

Alternatively, the DNA coding for an endo-1,3(4)-β-glucanase of the invention may, in accordance with well-known procedures, conveniently be isolated from DNA from any of the above mentioned organisms by use of synthetic oligonucleotide probes prepared on the basis of a DNA sequence disclosed herein. For instance, a suitable oligonucleotide probe may be prepared on the basis of the nucleotide sequence shown in SEQ ID No. 3, or at least a part of the nucleotide sequences shown in SEQ ID Nos. 1 and 2.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the endo-β-glucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endo-β-glucanase, the promoter and the terminator, respectively, and to insert them into suitable vectors are well known to persons skilled in the art (cf., for instance, Sambrook et al., *Molecular Cloning. A Laboratory Manual,* Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces sp., in particular *Saccharomyces cerevisiae, Saccharomyces kluyveri* or *Saccharomyces uvarum*, a strain of Schizosaccharomyces sp., such as *Schizosaccharomyces pombe,* a strain of Hansenula sp., or a strain of Pichia sp., or a strain of Yarrowia sp. such as *Yarrowia lipolytica,* or a strain of Kluyveromyces sp., such as *Kluyveromyces lactis.*

In a still further aspect, the present invention relates to a method of producing an enzyme according of the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed endo-β-glucanase may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In a still further aspect, the present invention relates to an enzyme preparation useful for the modification or degradation of β-glucan containing materials, said preparation being enriched with an enzyme exhibiting endo-1,3(4)-β-glucanase activity as described above.

The enzyme preparation having been enriched with an enzyme of the invention may e.g. be an enzyme preparation comprising multiple enzymatic activities, in particular an enzyme preparation comprising different enzyme activities required for the modification or degradation of microbial cell walls. Examples of such enzyme preparation includes lytic enzyme systems, in particular of microbial (fungal or bacterial) origin, e.g. derived from a strain of Trichoderma, such as *Trichoderma harzianum, Trichoderma viride* or *Trichoderma reesie,* a strain of Oerskovia sp., such as *Oerskovia xanthineolytica,* a strain of Arthrobacter sp. such as *Arthrobacter luteus,* a strain of Rhizoctonia sp. or Cytophaga sp., a strain of a Staphylococcus sp., or a strain of Streptomyces sp. Commercially available enzyme preparations which may conveniently be boosted with an enzyme of the invention includes Novozyme® 234, Cereflo® 200L, and Glucanex®, all available from Novo Nordisk A/S, Denmark, Cellulase (available from Merck), Cellulase OP and Cellulase CT (both available from Sturge), and/or Chitinase (available from Sigma).

In the context of uses according to the present invention, the term "enriched" is intended to indicate that the endo-1,3 (4)β-glucanase activity of the enzyme preparation has been increased, e.g. with an enrichment factor of at least 1.1, conveniently due to addition of an enzyme of the invention prepared by the method described above.

Alternatively, the enzyme preparation enriched with an enzyme with endo-1,3(4)-β-glucanase activity may be one which comprises an enzyme of the invention as the major enzymatic component, e.g. a mono-component enzy me epreparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

An enzyme preparation of the invention may, in addition to an endo-1,3(4)-β-glucanase of the invention, contain one or more other cell wall degrading enzymes, for instance those with cellulolytic, mannanolytic, chitinolytic or proteolytic activities such as cellulase, endo-glucanase, γ-glucosidases, β1,6-glucanase, mannanase, endo- or exo-chitinase, protease, α- or β-mannosidase or mutanase. The additional enzyme(s) may be producible by means of a microorganism belonging to the genus Aspergillus, preferably *Aspergillus niger, Aspergillus aculeatus, Aspergillus awamori* or *Aspergillus oryzae,* or Trichoderma or any of the microorganisms mentioned above in connection with the commercially available enzyme preparations.

Examples are given below of preferred uses of the enzyme preparation of the invention. The dosage of the enzyme preparaiation of the invention and other conditions under which the preparation is used may be determined on the basis of methods known in the art.

The enzyme preparation according to the invention may preferably be used as an agent for degradation or modification of β-glucan containing material such as microbial cell walls. In particular, the enzyme preparation of the invention may be used for rupturing or lysing cell walls of microorganisms thereby enabling recovery of desirable products produced by the microorganism.

It will be understood that the specific composition of the enzyme preparation to be used should be adapted to the composition of the cell wall to be ruptured or lysed. For instance, yeast cell walls have been found to comprise two main layers, an outer layer of protein-mannan complex and an inner glucan layer. In order to efficiently rupturing the cell wall of yeast it is desirable that the enzyme preparation comprises at least protease, mannanase and β-glucanase activity.

The extract recovered after rupture of the microbial cell walls normally comprises a number of different components, such as vitamins, colorants, flavourants, emulsifiers and stabilizers. Extracts obtained from rupture of yeast, i.e. yeast extracts, are used as such, e.g. for food or feed applications—or components thereof may be recovered and optionally further processed.

Examples of such products include emulsif iers, stabilizers, vitamins, colorants (e.g. carotenoids, Q-10 and astaxanthin), enzymes, proteins and flavour components or flavour enhancers (e.g. MSG, 5'-GMP and 5'-IMP). The products to be recovered may be inherent products of the microorganism in question, or may be products which the microorganism has been constructed to produce, e.g. recombinant products.

Further, the endo-1,3(4)-β-glucanase of the invention can be used for extracting mannan protein from the outer layer of yeast cell walls, such the cell wall of *Saccharomyces cerevisiae.* Manno-protein can be used as an effective bioemulsifier.

In addition, the enzyme preparation of the invention may be used in the production of protoplast from yeasts (e.g. of Saccnaromyces sp. or Schizosaccharomyces sp.) or from fungi (e.g. Aspergillus sp. or Penicillium sp.). Preparation and regeneration of protoplast from such organisms are important in fusion, transformation and cloning studies. The production of protoplasts may be performed in accordance with methods known in the art.

In addition, the enzyme preparation of the invention may be used in the modification of β-glucans, such as curdlan, laminarin and lichenan.

In a-still further aspect, the present invention relates to an enzyme preparation useful for the degradation or modification plant cell wall containing materials, said preparation being enriched in an enzyme with endo-1,3(4)-β-glucanase of the invention.

The enzyme preparation for degradation or modification of plant cell walls having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast® or Celluzyme™ (all available from Novo Nordisk A/S).

The enzyme preparation of the invention may, in addition to the endo-1,3(4)-β-glucanase of the invention, contain one or more other plant cell wall degrading enzymes, for instance those with cellulolytic, xylanolytic or pectinolytic activities such as xylanase, arabinanase, galactanase, rhamnogalacturonase, acetylesterase, galactanase, polygalacturonase, pectin lyase, pectate lyase, endoglucanase (e.g. of another specificity than the endo-1,3(4)-β-glucanase disclosed herein) or pectin methylesterase. These additional enzyme (s) may be producible by means of a microorganism belonging to the genus Aspergillus, preferably *Aspergillus niger, Aspergillus aculeatus, Aspergillus awalori* or *Aspergillus oryzae.*

The endo-1,3 (4)-β-glucanase according to the invention may also be produced essentially free from other cell wall degrading enzyme. This makes it possible to use the enzyme alone or together with other monocomponent enzymes to give the optimal combination of enzymes for a particular application. It is thereby possible to design enzyme combinations, which only degrade specific parts of the cell. This specific degradation has not previously been possible to obtain with commercially available cellulase, glucane, chitinase, mutanase, hemicellulase and/or pectinase preparations.

The endo-1,3(4)-β-glucanase of the invention has been found to have a high specificity towards β-1,3-glucans, a s well as towards mixed linkages β-1,3-1,4-glucans.

The activity towards mixed β-1,3-1,4 glucans makes the endo-1,3(4)-β-glucanase and homologues thereof useful for brewing and grape wine or press-juice making.

For brewing purposes the enzymes degrades the barley β-glucan and thereby reduces the viscosity and improves the filterability of the wort. In brewing the high specificity for β-glucans is an advantage as compared to other endoglucanases as the viscosity caused by β-glucan can be reduced without simultaneous degradation of the cellulose structures which are essential for the filterability of the wort where brewers spent grains act as filter-aid.

In connection with grape wine or press-juice making the endo-1,3(4)-β-glucanase can help improve the filterability by preventing growth of microorganisms, such as Botrytis cinerea, which may infect the grapes.

Furthermore, the activity towards mixed β-1,3-1,4 glucans makes the enzyme useful for processing of or for addition to food or feed to improve the feed-uptake and/or digestibility. Furthermore, the endo-1,3(4)-β-glucanase may be used to improve the quality of baked products or other cereal products.

The endo-1,3(4)-β-glucanase of the invention may also be used to produce oligosaccharides from e.g. plant material with mixed β-1,3-1,4 glucan. The resulting oligosaccharides may be used as bulking agents in e.g. food.

Furthermore, the endo-1,3(4)-β-glucanase may be used for extraction of aromatic compounds from plant materials.

For the above uses, the dosage of the enzyme preparation of the invention and other conditions under which the preparation is used may be determined on the basis of methods known in the art.

Also contemplated according to the invention is the use of endo-1,3(4)-β-glucanase or enzyme preparation thereof as an active ingredient in cleaning compositions for dentures. The composition is capable of removing microorganisms from the surface of dentures.

Also the use in plaque removing compositions, in e.g. mouth washes is contemplated. Plaque are formed on the surface of teeth is composed mainly of polysaccharides. They stick to the surface of the teeth and the microorganisms present in the mouth. The endo-1,3(4)-β-glucanase of the invention may in this context be use in combination with other glucanases such as mutanase and dextranase.

Also biofilms formed on the surface of e.g. contact lens cases can be removed by the action of glucanases, including the endo-1,3(4)-β-glucanases of the invention.

Further molds on coatings may also be removed by the use of compositions comprising the endo-1,3(4)-β-glucanase of the invention.

Also contemplated is the use of the endo-1,3(4)-β-glucanase of the invention as an anti-fungal agent.

In connection with removal of excess dye from textiles the endo-1,3(4)-β-glucanase of the invention can also be used advantageously.

The invention is described in further detail in the following examples which are not in any way intended to limit the scope of the invention as claimed.

MATERIALS AND METHODS

Donor organism: mRNA was isolated from Trichoderma harzianum, CBS 243.71, grown in a maize grits-containing fermentation medium with agitation to ensure sufficient aeration. Mycelia were harvested after 3–5 days' growth, immediately frozen in liquid nitrogen and stored at −80° C.

Yeast strains: The Saccharomyces cerevisiae strain used was yNG231 (MAT alpha, leu2, ura3-52, his4-539, pep4-delta 1, cir+) or JG169 (MATα; ura 3-52; leu 2-3, 112; his 3-D200; pep 4-1137; prc1::HIS3; prb1:: LEU2; cir+).

Deposited organism: Saccharomyces cerevisiae NN049006 is transformed with a DNA sequence, comprising the two partial DNA sequences shown in SEQ ID No. 5 and SEQ ID No. 6, comprised in the expression plasmid pYES 2.0. The transformed DNA sequence is homologous with the sequence shown in SEQ ID No. 3.

Isolation of the the DNA sequence shown in SEQ ID Nos. 5 and 6 The yeast expression vector pYES 2.0 containing the cDNA sequences derived from Acremonium sp. shown in SEQ ID Nos. 5 and 6, can be isolated from the deposited organism Saccharomyces cerevisiae NN049006 by extraction of plasmid cDNA by methods known in the art.

The deposited organism may be cultured on agar plates containing SC+2% galactose and incubated at 30° C. for 3–5 days as described below.

Plasmids: The expression plasmid pYHD17 containing the yeast TPI promoter was prepared from the commercially available plasmid pYES 2.0 (Invitrogen). The plasmid and the construction thereof is further described in WO 93/11249, the contents of which is hereby incorporated by reference.

The Aspergillus expression vector pHD414 is a derivative of the plasmid p775 (described in EP 238 023). The construction of pHD414 is further described in WO 94/14952.

pYES 2.0 (Invitrogen)

Extraction of total RNA: The total RNA was prepared by extraction with guanidinium thiocyanate followed by ultracentrifugation through a 5.7 M CsCl cushion essentially as described by Chirgwin et al., 1979 and in WO 94/14952.

Isolation of poly(A)$^+$ RNA: The poly(A)$^+$ RNAs were isolated by oligo (dT)-cellulose affinity chromatography using the procedure described in WO 93/11249.

cDNA synthesis and modification: Double-stranded cDNA was synthesized from 5 µg of poly(A)$^+$ RNA by the RNase H method (Gubler & Hoffman 1983, Sambrook et al., 1989) using the hair-pin modification. The synthesis of double stranded cDNA was carried out as described earlier in WO 95/02044, except that 25 ng of random hexanucleotide primers (Gibco BRL, USA) were added to the first strand synthesis reaction mixture. After having been treated with Mung bean nuclease (Bethesda Research Laboratories), the ds cDNA was made blunt-ended with T4 DNA polymerase (Invitrogen) and the cDNA was ligated to non-palindromic BstX I adaptors (Invitrogen) in accordance with the manufacturers instructions.

Construction of cDNA libraries: The adapted, ds cDNA was recovered by centrifugation, washed in 70% EtOH and resuspended in 25 ml distilled water. Prior to large-scale library ligation, four test ligations were carried out in 10 µl of ligation buffer (same as above) each containing 1 µl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either pYES 2.0 vector Invitrogen or yHD13). The ligation reactions were performed by incubation at 16° C. for 12 h, heated at 70° C. for 5 min, and 1 µl of each ligation electroporated (200Ω, 2.5 kV, 25 µF) to 40 µl competent E. coli MC1061 cells (OD600=0.9 in 1 liter LB-broth, washed twice in cold distilled water, once in 20 ml of 10% glycerol, resuspended in 2 ml 10% glycerol). After addition of 1 ml SOC to each transformation mix, the cells were grown at 37° C. for 1 h, 50 µl plated on LB+ampicillin plates (100 µg/ml) and grown at 37° C. for 12 hours.

Using the optimal conditions a large-scale ligation was set up in 40 µl of ligation buffer containing 9 units of T4 ligase, and the reaction was incubated at 16° C. for 12 h. The ligation reaction was stopped by heating at 70° C. for 5 min, ethanol precipitated at −20° C. for 12 h, recovered by centrifugation and resuspended in 10 μl distilled water. One μl aliquots were transformed into electrocompetent *E. coli* 1061 cells using the same electroporation conditicns as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of yeast libraries: To ensure that all the bacterial clones were tested i n yeast, a number of yeast transformants 5 times larger than the number of bacterial clones in the original pools was set as the limit.

One μl aliquots of purified plasmid DNA (100 ng/μl) from individual pools were electroporated (200Ω, 1.5 kV, 25 μF) into 40 μl competent *S. cerevisiae* JG 169 cells (OD600=1.5 in 500 ml YPD, washed twice in cold distilled water, once in cold 1 M sorbitol, resuspended in 0.5 ml 1 M sorbitol, Becker & Guarante, 1991). After addition of 1 ml 1M cold sorbitol, 80 μl aliquots were plated on SC+glucose−uracil agar plates to give 250–500 c.f.u./plate and incubated at 30° C. for 3–5 days.

Identification of positive colonies: After 3–5 days of growth, the agar plates were replica plated onto several sets of SC+galactose−uracil agar plates. one set of plates containing 0.1% AZCL-curdlan or AZCL-β-glucan was then incubated for 3–5 days at 30° C. to detect for endo-1,3(4)-β-glucanase activity. Positive colonies were identified as colonies surrounded by a blue halo.

Cells from enzyme-positive colonies were spread for single colony isolation on agar, and an enzyme-producing single colony was selected for each of the endo-1,3(4)-β-glucanase-producing colonies identified.

Characterization of positive clones: The positive clones were obtained as single colonies, the CDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical).

Isolation of a cDNA gene for expression in Aspergillus: One or more endo-1,3(4)-β-glucanase-producing colonies was inoculated into 20 ml YPD broth in a 50 ml glass test tube. The tube was shaken for 2 days at 30° C. The cells were harvested by centrifugation for 10 min. at 3000 rpm.

The cells were resuspended in 1 ml 0.9 M sorbitol, 0.1 M EDTA, pH 7.5. The pellet was transferred to an Eppendorf tube, and spun for 30 seconds at full speed. The cells were resuspended in 0.4 ml 0.9 M sorbitol, 0.1 M EDTA, 14 mM β-mercaptoethanol. 100 μl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5 M EDTA pH 8.0, 0.6 ml 2 M Tris-Cl pH 8.0, 0.6 ml 10% SDS) was added, and the suspension was incubated at 65°0 C. for 30 minutes. 80 μl 5 M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 μl TE and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μg/ml.

The DNA was transformed into *E.coli* by standard procedures. Plasmid DNA was isolated from *E.coli* using standard procedures, and analyzed by restriction enzyme analysis. The CDNA insert was excised using appropriate restriction enzymes and ligated into an Aspergillus expression vector.

Transformation of *Aspergillus oryzae* or *Aspergillus niger* (general procedure): 100 ml of YPD (Sherma n et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6 M $MgSO_4$. The mycelium is suspended in 15 ml of 1.2 M $MGSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifugation is performed for 15 minutes at 100 g and the protoplasts are collected from the top of the $MgSO_4$ cushion. 2 volumes of STC (1.2 M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates (Cove Biochem.Biophys.Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* transformants Each of the transformants were inoculated in 10 ml YPM and propagated. After 2–5 days of incubation at 37° C., 10 ml supernatant was removed. The endo-1,3(4)-β-glucanase activity was identified by AZCL-curdlan or AZCL-β-glucan.

Hybridization conditions (to be used in evaluating property i) of the DNA construct of the invention): Suitable conditions for determining hybridization between an oligonucleotide probe and an "analogous" DNA sequence involves presoaking the filter containing the DNA sequences to hybridize in 5×SSC and prehybridizing for 1 h at ~50° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~50° C. followed by washing three times in 2×SSC, 0.2% SDS at 50° C. for 30 minutes.

A suitable oligonucleotide probe to be used in the hybridization may be prepared on the basis of any of the DNA sequences shown in SEQ ID No 3, or at least a part of SEQ ID No. 1 or 2, or SEQ ID Nos. 5 or 6.

Immunological cross-reactivity: Antibodies to be used in determining immunological cross-reactivity may be prepared by use of a purified endo-1,3(4)-β-glucanase. More specifically, antiserum against the endo-1,3(4)-β-glucanase of the invention may be raised by immunizing rabbits (or other rodents) according to the procedure described by N. Axelsen et al. in: *A Manual of Ouantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation ($(NH_4)_2 SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Coomassie staining: The gel is carefully removed from the glass plates and incubated on a slowly rotating shaking table in approximately 100 ml of the following solutions:

1) 30 min in 40% v/v ethanol; 5% v/v acetic acid
2) 30 min in 40% v/v ethanol; 5% v/v acetic acid+0.1% Coomassie Brilliant Blue R250
3) Destaining in 30 min in 40% v/v ethanol; 5% v/v acetic acid until background is sufficiently reduced.
4) Finally the gel is incubated in preserving solution: 5% v/v acetic acid; 10% v/v ethanol; 5% v/v glycerol and air dried between two sheets of cellophane membrane.

Silver staining: The gel is carefully removed from the glass plates and incubated on a slowly rotating shaking table in approximately 100 ml of the following solutions:

1) 30 min in 40% v/v ethanol; 5% v/v acetic acid
2) 20 min in 10% v/v ethanol; 5% v/v acetic acid
3) 20 min in 0.0057% w/v APS (0,25 mM)
4) 60 min in 0.1% w/v $AgNO_3$
5) For development, the gel is dipped in developer: 0,015% formaldehyde; 2% w/v $Na_2CO_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10× Basal salt: 75 g yeast nitrogen base, 113 g succinic acid, 68 g NaOH, $H_2O$ ad 1000 ml, sterile filtered.

SC-URA: 100 ml 10× Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-URA agar: SC-URA, 20 g/l agar added.

AZCL-curdlan (Megazyme, Australia)

AZCL-β-glucan (Megazyme, Australia)

Qiagen purified plasmid DNA (Qiagen, USA),

Sequenase®kit (U.S. Biochemical corp., USA)

Random hexanucleotide primers (Gibco BRL, USA)

EXAMPLE 1

An *E. coli* library from *T. harzianum* consisting of approx. $10^6$ individual clones in 150 pools was constructed.

DNA was isolated from 20 individual clones from the library and subjected to analysis for cDNA insertion. The insertion frequency was found to be >90%. DNA from some of the pools was transformed into yeast, and 50–100 plates containing 200–500 yeast colonies were obtained from each pool.

Positive colonies were identified and isolated on agar. cDNA inserts were amplified directly from the yeast colony and characterized as described in the Materials and Methods section above. The cDNA sequence encoding the endo-1,3 (4)-β-glucanase is shown in SEQ ID No. 3.

EXAMPLE 2

Total DNA was isolated from a yeast colony and plasmid DNA was rescued by transformation of *E. coli* as described above. In order to express the endo-1,3(4)-β-glucanase in Aspergillus, the DNA was digested with HindIII/XbaI, size fractionated on gel, and a fragment corresponding to the endo-1,3(4)-β-glucanase gene was purified. The gene was subsequently ligated to HindIII/XbaI digested pHD414.

After amplification of the DNA in *E. coli* the plasmid pA2CU3 was transformed into *Aspergillus oryzae* as described above.

Test of *A. oryzae* transformants

Each of the transformants were tested for endo-1,3(4)-β-glucanase activity as described above. Some of the transformants had endo-1,3(4)-β-glucanase activity which was significantly larger than the *Aspergillus oryzae* background. This demonstrates efficient expression of the endo-1,3(4)-β-glucanase in *Aspergillus oryzae*. The transformant with the highest endo-1,3(4)-β-glucanase activity was selected and inoculated in a 500 ml shake flask with YPM media. After 3–5 days of fermentation with sufficient agitation to ensure good aeration, the culture broth was centrifuged for 10 minutes at 2000 g and the supernatant recovered.

EXAMPLE 3

Purification of endo-1,3(4)-β-glucanase)

The culture supernatant from fermentation of *Aspergillus oryzae* or *A. niger* expressing endo-1,3(4)-β-glucanase was centrifuged and filtered through a 0.2 µm filter to remove the mycelia.

35–50 ml of the filtered supernatant (5–50 mg recombinant enzyme) was ultrafiltrated in an Amicon ultrafiltration device with a 10 kDa membrane to achieve 10 fold concentration.

This concentrate was diluted 100 times in 25 mM Tris pH 8.0 in two successive rounds of ultrafiltration in the same device. This ultrafiltrated sample was loaded at 1.5 ml/min on a Pharmacia XK16/10 Fast Flow Q Sepharose anion exchanger equilibrated in 25 mM Tris pH 8.0. After the sample was applied, the column was washed with two column volumes 25 mM Tris pH 8.0, and bound proteins were eluted with a linear increasing NaCl gradient from 0 to 0.5 M NaCl in 25 mM Tris pH 8.0.

5 ml fractions were collected and assayed for endo-1,3 (4)-β-glucanase activity as described. Endo-1,3(4)-β-glucanase eluted at approximately 0.1 M NaCl. Endo-1,3 (4)-β-glucanase eluted from the column was not pure.

Thus, the endo-1,3(4)-β-glucanase containing fractions were pooled and concentrated by ultrafiltration in Amicon ultrafiltration device with a 10 kDa membrane to achieve 10 fold concentration. This concentrate was diluted 100 times in 10 mM sodium phosphate pH 6.8 in two successive rounds of ultrafiltration in the same device. This ultrafiltrated sample was loaded at 1 ml/min on a Pharmacia XK10/20 column packed with BioGel HTP (BioRad, USA) equilibrated in 10 mM sodium phosphate pH 6.8. After the sample had been applied, the column was washed with two column volumes 10 mM sodium phosphate pH 6.8 and bound proteins were eluted with a linear increasing concentration of sodium phosphate from 0.01 to 0.5 M. 5 ml fractions were collected and assayed for endo-1,3(4)-β-glucanase activity. The endo-1,3(4)-glucanase was not retained on the column under these conditions, and the fractions containing endo-1,3(4)-β-glucanase was concentrated in a Filtron Macrosep 10 kDa device to a final volume of 3 ml. This sample was loaded on a Pharmacia Superdex G75 column equilibrated in 0.25 M ammonium acetate pH 5.5 at a flow of 1 ml/min. 5 ml fractions were collected and assayed for endo-1,3(4)-β-glucanase activity. The endo-1,3 (4)-β-glucanase eluted from this column was more than 50% pure as judged by SDS PAGE and used for the subsequent characterization.

EXAMPLE 4
Mw determination by SDS-PAGE Electrorhoresis

SDS-PAGE electrophoresis was performed in a Mini-Leak 4 electrophoresis unit (Kem-En-Tec, Copenhagen) as a modified version of the Laemli procedure (Laemmli 1970; Christgau, Schierbeck et al. 1991). Briefly, the separation gel was cast with 12% acrylamide; 0.2% BIS acrylamide; 0.1% SDS; 0.375 M Tris pH 8.8; 0.04% APS (ammonium-persulphate) & 0.04% TEMED. After 6–15 hours polymerization the stacking gel was cast with 4.5% w/w Acrylamide; 0.075% BIS-acrylamide; 0.1% SDS; 66.5 mM Tris pH 6.8; 0.4% w/w APS (ammonium-persulphate) & 0.4% TEMED. The electrode chambers were filled with running buffer: 25 mM Tris-base; 0.192 M glycine & 0.05% SDS, whereafter the samples, containing sample buffer were loaded, and the gel was run at 2–4 mA/gel for over-night running and 10–30 mA/gel for fast running, whereafter the gel was removed and stained by either coomassie or silver staining as described above in the Materials and Methods section.

The apparent molecular weight (Mw) was found to be about 31 kDa.

EXAMPLE 5
pI Determination by Isoelectric Focusing

Isoelectric focusing is carried out on Ampholine PAG plates pH 3,5–9,5 (Pharmacia, Upsala) on a Multiphor electrophoresis unit according to the manufactures instructions. After electrophoresis the gel was either commassie stained or silver stained as described above, except that prior to staining, the gel was incubated for 20 min in 20% TCA (Tri-chloro-acetic acid).

The apparent pI was around 5.1.

EXAMPLE 6
pH Optimum

Buffers of pH values between 2.5 and 8.0 were made by mixing 0.1M Tri-sodium phosphate with 0.1M citric acid. Endo-β-1,3(4)-glucanase was diluted to ensure the assay response to be within the linear range of the assay. The substrate was a 0.4% suspension of AZCL-β-glucan (MegaZyme) mixed 1:1 with the citrate/phosphate buffer to a final substrate concentration of 0.2% AZCL-β-glucan. 1 ml substrate in Eppendorf® 1.5 ml polypropylene tubes were added 10 μl of enzyme solution and incubated for 15 minutes in Eppendorf® temperature controlled Thermomixers before heat-inactivation of enzymes for 20 minutes at 95° C. in a separate Thermomixer. The tubes were centrifuged and 200 μl of each supernatant was transferred to a well in a 96 well microtiter plate and OD was measured at 620 nm in an ELISA reader (Labsystems Multiskan® MCC/340).

For the pH optimum incubations took place at 30° C. For each pH value, three tubes were added enzyme and incubated before heat-inactivation, whereas one tube (the blank) was added enzyme and heat-inactivated immediately. The mean value of the three sincubated samples was calculated and the blank value was substracted. The value at optimal pH was defined as 100%.

The activity of the endo-β-1,3(4)-glucanase as a function of pH at 30° C. is shown in FIG. 1. It is seen that the endo-β-1,3(4)-glucanase has more than 60% activity between pH 4.0 and 6.5 and optimal activity at pH 4.5–5.5.

EXAMPLE 7
Temperature Optimum

For the temperature optimum incubations took place as described above in pH 5.0 citrate/phosphate buffer. The temperatures ranged from 30° C. to 80° C. For each temperature three incubations were carried out and the mean calculated. Three blanks were produced by immediate heat-inactivation of enzymes and the mean was subtracted from the incubated sample values. The activity at the optimal temperature was defined as 100%.

Figure 2:
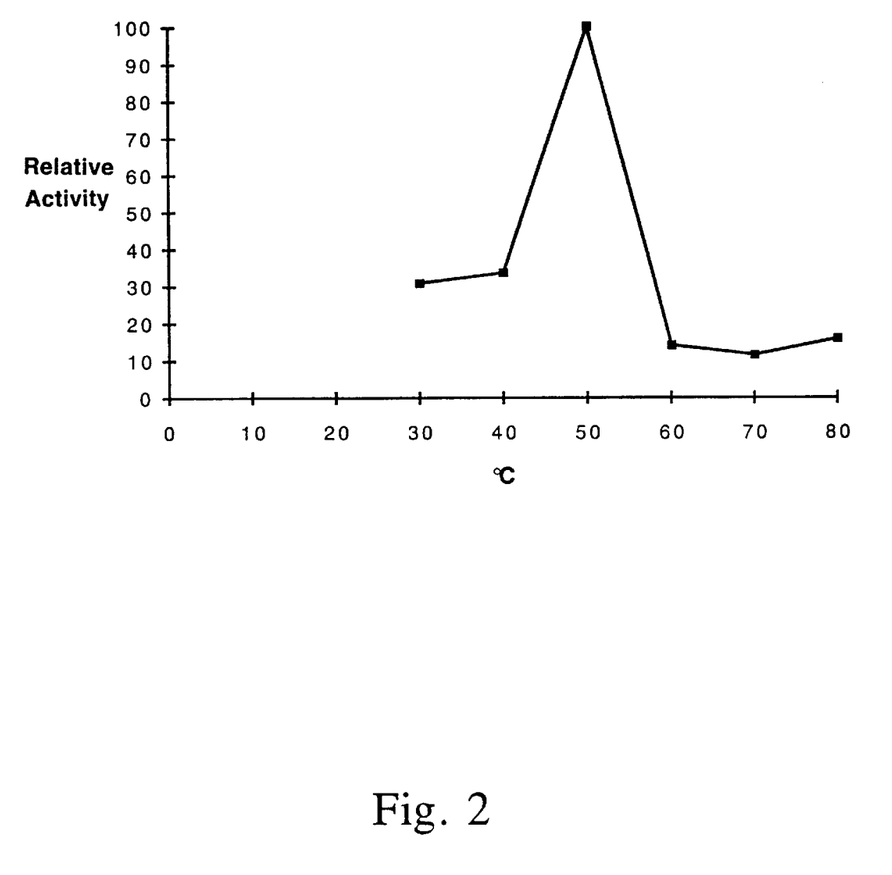
FIG. 2 shows the activity of the endo-β-1,3(4)-glucanase of the invention as a function of the temperature at pH 5.0.

The activity of the endo-β-1,3(4)-glucanase as a function of temperature at pH 5.0 is shown in FIG. 2. It is seen that the endo-β-1,3(4)-glucanase has optimal activity at 50° C.

EXAMPLE 8
Kinetic Parameters $K_m$ and specific activity were determined by carrying out incubations at 30° C. for 15 minutes at β-1,3-1,4-glucan (MegaZyme) concentrations (S) ranging from 0.025 to 1.5% in citrate/phosphate buffer pH 5.0. The reaction rate (v) was measured as the formation of reducing sugar/minute. The concentration of reducing sugars after inactivation of enzyme were determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Glucose was used as a standard and blanks were subtracted. Then S/v was depicted as a function of S, and linear regression analysis was carried out. The slope (=$1/V_{max}$) and the intercept ($K_m/V_{max}$) was used to calculate the Km and the specific activity (=Vmax/E), where E was the amount of enzyme added. The specific activity was measured as U/mg of enzyme where 1U=1 μmol reducing sugar/minute.

The specific activity of the endo-β-1,3(4)-glucanase at 30° C. pH 5.0 was around 100–200 U/mg enzyme and Km was around 0.02–0.06% β-1,3–1,4-glucan.

EXAMPLE 9
Depolymerization of β-qlucans

For gelfiltration chromatography 1 ml aliqouts of 1% solutions of pustulan (Roth), laminarin (Sigma), curdlan (MegaZyme) or β-1,3–1,4-glucan (MegaZyme) were incubated with 10 µl of 0.2 mg/ml enzyme solution at 30° C. for 0, 1, 2, 4, and 24 hours before heat-inactivation. 25 µl of sample was injected into three TSK-columns (TosoHaas) in series (PW G4000, PW G3000, PW G2500) and saccharides were eluted with 0.4 M acetate buffer pH 3.0 at 0.8 ml/min. Eluting saccharides were determined by a Shimadzu RI detector and collection of data was commenced 15 minutes after injection. Data were processed by Dionex software. Dextrans (from Serva) were used as molecular weight standards.

Figure 3:
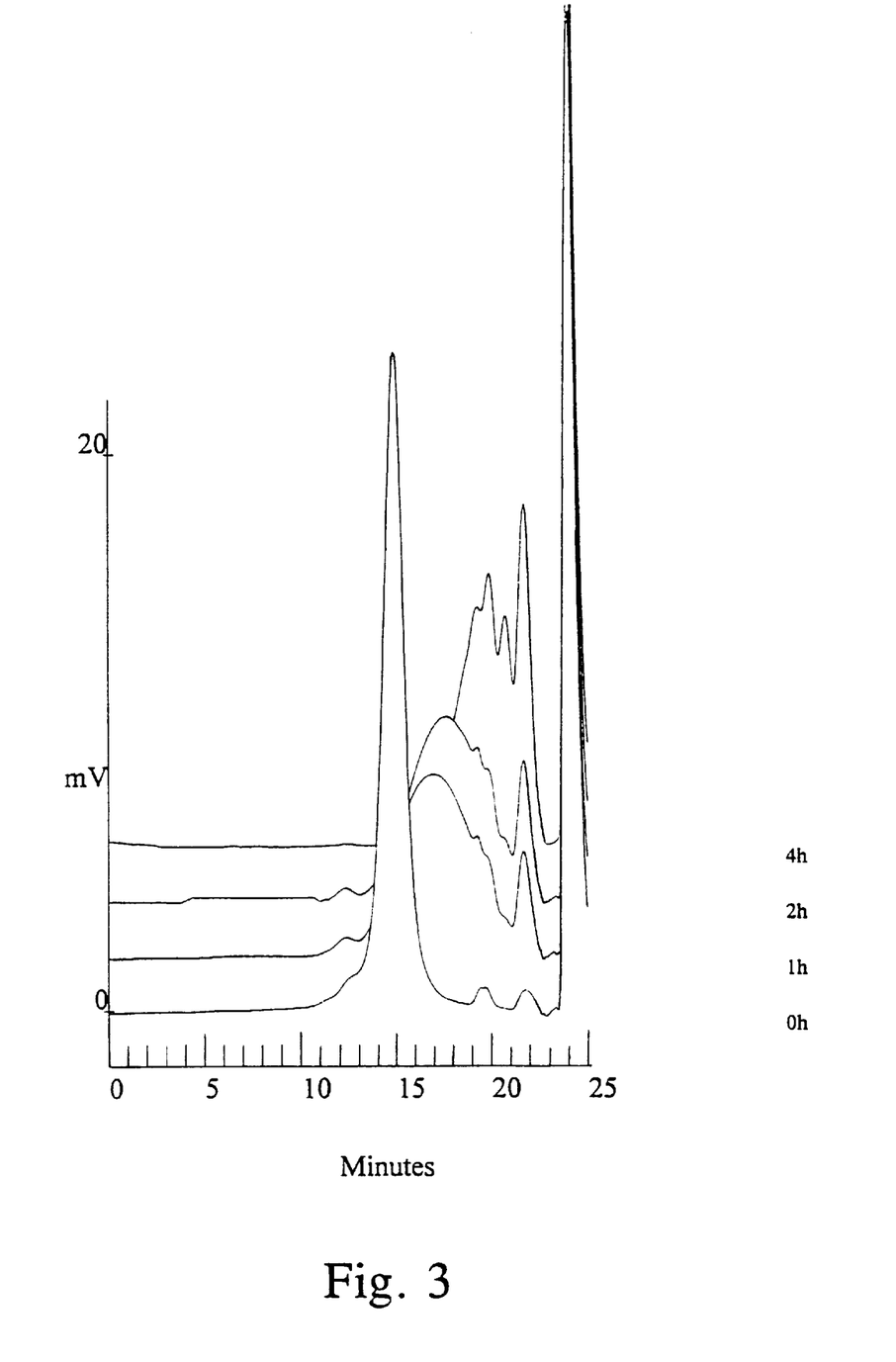
FIG. 3 shows the depolymerisation of Laminarin by the endo-1,3(4)-β-glucanase of the invention.
Figure 4:
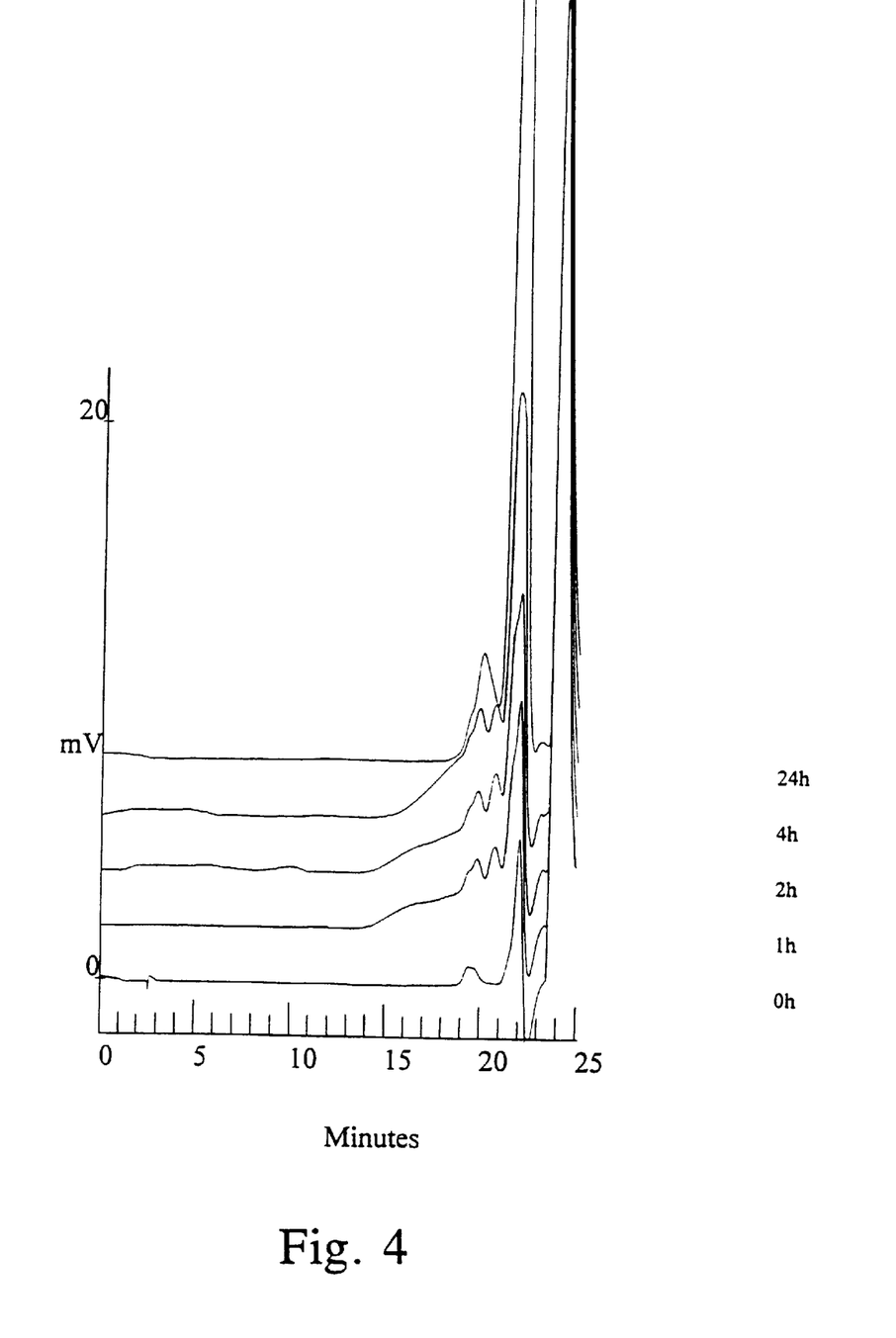
FIG. 4 shows the depolymerisation of β-1,3-1,4-glucan by the endo-1,3(4)-β-glucanase of the invention.
Figure 5:
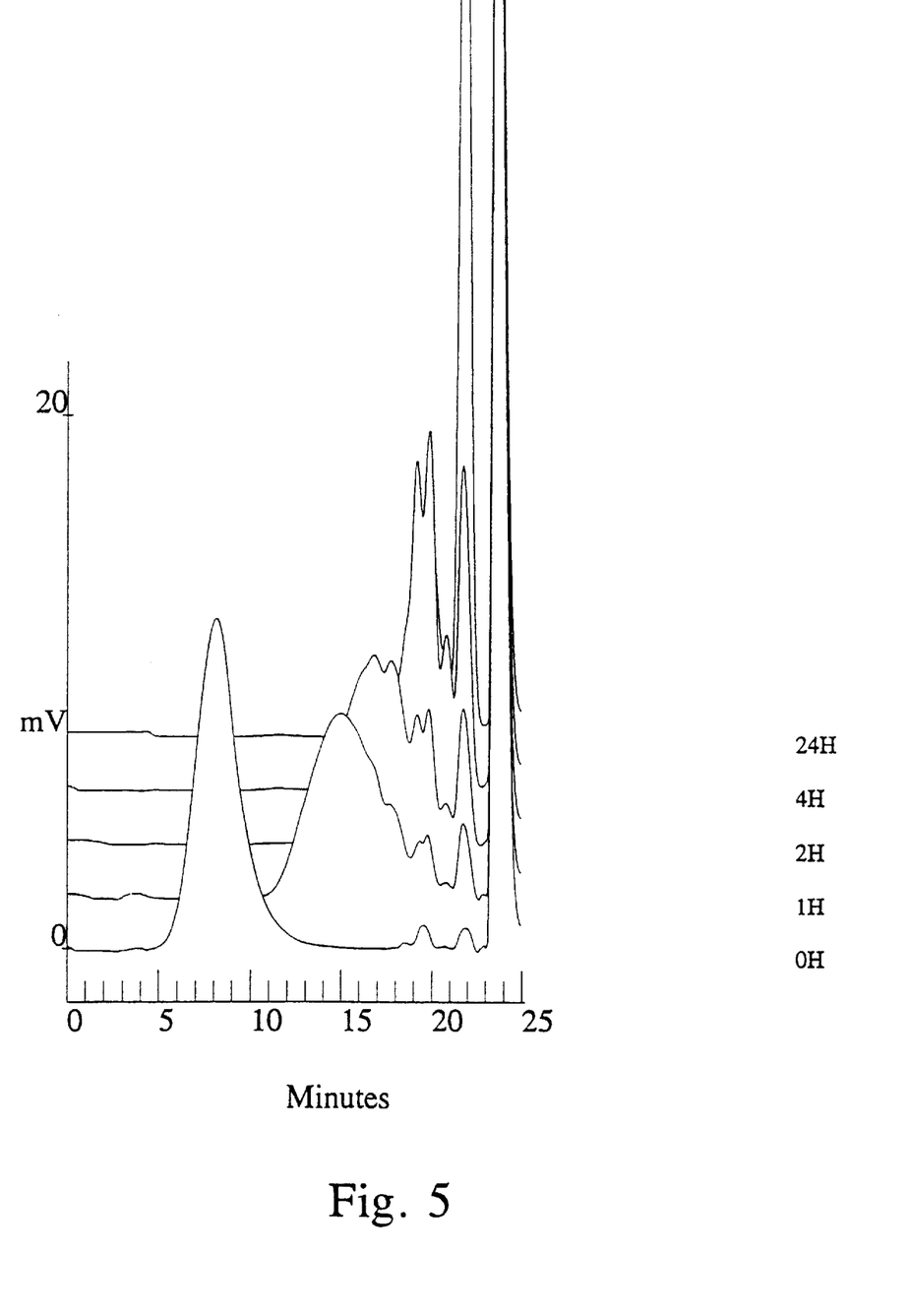
FIG. 5 shows the depolymerisation of curdlan by the endo-1,3(4)-β-glucanase of the invention.

In accordance with the definition of endo-β-1,3(4)-glucanase activity the enzyme degraded readily the laminarin (see FIG. 3), β-1,3-glucan (curdlan) (FIG. 4) and β-glucan from oat (β-1,3-1,4-glucan) (FIG. 5), whereas the pustulan was not degraded.

Figure 6:
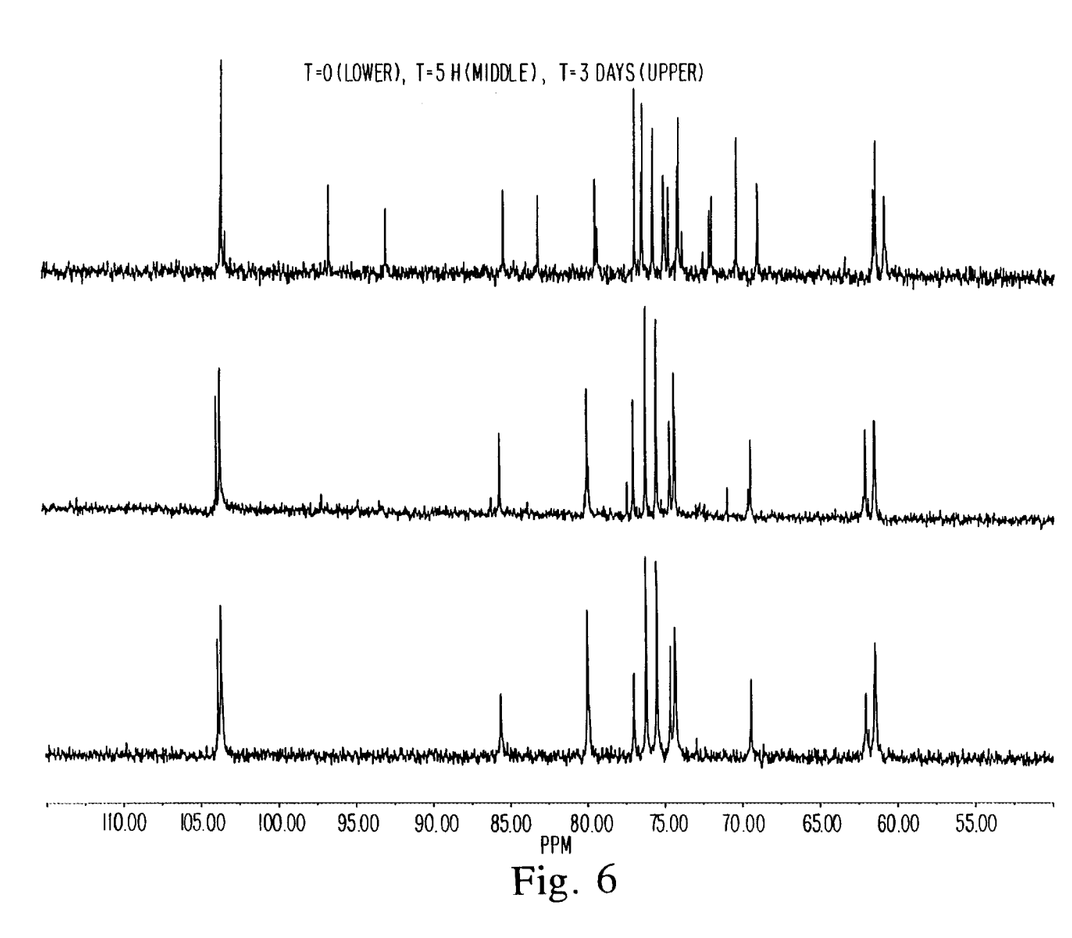
FIG. 6 shows the $^{13}C$ NMR spectra of β-glucan before, during and after treatment with endo-1,3(4)-β-glucanase of the invention.

EXAMPLE 10
Digestion of β-qlucan with endo-1,3(4)-≈-glucanase $^{13}$C NMR spectra were recorded on a Brucker AC300 spectrometer operating at 75.47 MHz. Spectra were recorded at 330 K and data accumulated over-night.

β-1,3-1,4-glucan (10 mg) was dissolved in D$_2$O (1000 µl, 99.95% D (Merck)), and the $^{13}$C NMR spectrum recorded (FIG. 6, lower trace). Endo-1,3(4)-glucanase solution (10 µl, 0.070 mg protein/ml) was added, and after keeping the mixture for 5 hours at room-temperature the $^{13}$C-NMR spectrum was recorded again (FIG. 6, middle trace). A second portion of enzyme solution (10µ) was added and the reaction was allowed to proceed for 3 days at room-temperature. Subsequently, the $^{13}$C NMR spectrum of the reaction mixture was acquired (FIG. 6, upper trace).

The spectrum recorded for β-glucan was essentially identical to the one reported (Bock et al., (1991), Carbohydrate Research, 211, 219–233)). The spectrum acquired after 5 hours incubation with endo-1,3(4)-β-glucanase showed that only minor digestion of the substrate had taken place. However, after 3 days signals corresponding to anomeric carbon atoms resonating at 96.7 (C-1β) and 93.0 ppm (C-1α) were present. Furthermore, a signal assignable to C-3 in 3-glucosylated units was unchanged, which indicates that 1,3-linkages were not hydrolysed by the enzyme. These results verify that the enzyme is an endo-1,3(4)-β-glucanase (E.C. 3.2.1.6) which in addition to the β-1,3-linkage in β-1,3-glucan also hydrolyses a β-1,4 linkage in mixed linkage β-1,3-1,4-glucans.

EXAMPLE 11

Construction and screening of Acremonium sp. cDNA library

Total RNA was prepared from frozen, powdered mycelium of the Acremonium sp. CBS 265.95 strain by extraction with guanidinium thiocyanate followed by ultracentrifugation through a 5.7 M CsCl cushion (Chirgwin et al., (1979), Biochemistry, 18, 5294–5299). Poly(A)+RNA was isolated by oligo(dT)cellulose affinity chromatography (Aviv and Leder, (1972), Proc. Natl. Acad. Sci. U.S.A., 69, 1408–1412). Double-stranded cDNA was synthesized from 5 µg of poly(A)+RNA as described (Gubler and Hoffman, (1983), Gene, 25, 263–269; Sambrook et al., (1989), Molecular Cloning: A Laboratory Manual. Cold Spring Harbor, N.Y., Cold Spring Harbot Laboratory) except that 25 ng of random hexanucleotide primers (Gibco BRL, USA) were included in the first strand synthesis. A cDNA library consisting of 1.5×10$^6$ clones was constructed in the yeast expression vector pYES 2.0 as described previously (Kofod et al., (1994), J. Biol. Chem., 261, 8407–8413). Plasmid DNA from a cDNA library pool was transformed into S. cerevisiae W3124 (van den Hazel et al., (1992), Eur. J. Biochem., 207, 277–283) by electroporation (Becker and Guarente, (1991), Methods Enzymol., 194, 182–187) and the transformants were plated on SC agar (Sherman, (1991), Methods Enzymol. 194, 3–21) containing 2% glucose. After incubation at 30° C. for 3 to 4 days, the colonies were replicated onto SC agar plates containing 2% galactose and incubated for 3 days at 30° C. The enzyme activity of the transformed S. cerevisiae was checked on AZCL-β-glucan and AZCL-curdlan. Endo-1,3(4)-glucanase positive clones were identified.

Total DNA from the positive yeast colonies was isolated and the insert containing pYES 2.0 clones were rescued by transformation of E. coli MC 1061 (Meissner et al., (1987), Proc. Natl. Acad. Sci. U.S.A., 84, 4171–4176) to ampicillin resistance.

Nucleotide Sequence Analysis

The nucleotide sequence of the cDNA insert was determined from both strands by the dideoxy chain termination method (Sanger et al., (1977), Proc. Natl. Acad. Sci. U.S.A., 74, 5463–5467) using Qiagen purified plasmid DNA, the Sequenase® kit or synthetic oligonucleotide primers. Analysis of the sequence date were performed according to Devereux et al., (1984), Nucleic Acids Res. , 12, 387–395). Two partial cDNA sequence are shown in SEQ ID Nos. 5 and 6.

EXAMPLE 12
Hydrolysis Trials on Isolated Yeast Cell Wall Material 450 g og Bakers yeast, Saccharomiyces cerevisiae, was suspended in 1350 g of water. A plasmolysis was carried out under stirring at 50° C. for 18 hours. 10 ml samples were taken at the time 0, 0.5 h, 1 h, 17 h, 17.5 h and at 18 h. The samples were centrifuged on a Labofuge centrifuge from Heraeus at 3400×g (equivalent to 4500 rpm on the used centrifuge) for 5 minutes. The reaction was followed by measurements on the supernatant of the osmolality using a Advanced Wide-Range Osmometer 3W2 (Advanced Instruments). A DUR REFRACTQMETER-Electronic (Schmidt Haensch) was used for testing of the dry matter content of these centrifugates. The data shown in table 1 was found:

TABLE 1

Data measured during the plasmolysis of bakers yeast.

| Time (h) | Osmolality, mOSM/kg | ° BRIX |
|---|---|---|
| 0 | 115 | 0.6 |
| 0.5 | 165 | 0.8 |
| 1 | 196 | 0.9 |
| 17 | 350 | 4.5 |
| 17.5 | 354 | 4.6 |
| 18 | 356 | 4.6 |

After 18 h the whole content was centrifuged at 4500 rpm using a Sorvall RC-3G refrigerated centrifuge for 30 minutes. 1475.8 g of supernatant and 227.3 g of solid phase was collected. The solid was suspended in 1475.8 g of water and centrifuged again at 4500 rpm using a Sorvall RC-3G refrigerated centrifuge for 30 minutes. Finally 266.1 g of wa shed cell wall material was collected.

A dry matter determination was carried out at 105° C. over night. A content of 22.8% w/w dry matter was found. This material is called isolated cell wall material from yeast.

A blank hydrolysis trial was carried out by use of 21,9 g of isolated wet cell wall material, which material was suspended ad 70 ml water in a 250 ml Erlenmeyer flask. pH was adjusted to pH=5.0 by use of 6 N HCl. The total content in the Erlenmeyer flask was adjusted to 100 ml. Samples were taken at t=1, 5, 10, 20, 30, 60, 90, 120, 180, 240 minutes. The samples were immidiately centrifuged on a Labofuge centrifuge from Heraeus at 3400×g (equivalent to 4500 rpm on the used centrifuge) for 5 minutes. The reaction was followed by measurements on the supernatant of the osmolality using a Advanced Wide-Range Osmometer 3W2 (Advanced Instruments). The DUR REFRACTOMETER-Electronic was used for testing of the dry matter content of these centrifugates.

A hydrolysis trial was carried out as above but after the pH adjustment the total content in the Erlenmeyer flask was adjusted to 95 ml. After termostatting, approxamanly 2.5 mg endo-1,3(4)-β-glucanase was added. The hydrolysis reaction was carried out at 50° C. under magnet-stirring with the Erlemeyer flask placed in a water bath. Samples were taken and measured as above.

The data shown in table 2 was found for the blank hydrolysis and the endo-1,3(4)-β-glucanase treated yeast cell wall material.

TABLE 2

Solubilizing and degrading effect of endo-1,3(4)-β-glucanse

| | Blank | | | Endo-1,3(4)-β-glucanase treatment | | |
|---|---|---|---|---|---|---|
| Time, min. | mOSM/-kg | ΔmOSM/-kg | °BRIX | mOSM/kg | ΔmOSM/-kg | °BRIX |
| 1 | 20 | 0 | 0 | 37 | 0 | 0 |
| 5 | 20 | 0 | 0 | 37 | 0 | 0 |
| 10 | 21 | 1 | 0 | 38 | 1 | 0 |
| 20 | 21 | 1 | 0 | 41 | 4 | 0.10 |
| 30 | 22 | 2 | 0 | 43 | 6 | 0.14 |
| 60 | 23 | 3 | 0 | 50 | 13 | 0.30 |
| 90 | 24 | 4 | 0 | 58 | 21 | 0.46 |
| 120 | 26 | 6 | 0 | 64 | 27 | 0.56 |
| 180 | 28 | 8 | 0 | 76 | 39 | 0.74 |
| 240 | 30 | 10 | 0 | 85 | 48 | 0.84 |

REFERENCES

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Pitson et al., Noncellolytic fungal β-glucanases: Their physiology and regulation. In Enzyme Microb. Technol., 1993, vol. 15, March Reed and Nagodawithana, in Yeast Technology, Second Edition, pp. 372–380

Phaff, H. J., Enzymatic Yeast Cell Wall Degradation. In Food Proteins, Improvement through Chemical and Enzymatic Modification, edited by Feeney and Whitaker, Washington, 1977

Hamlyn et al., Efficient protoplast isolation from fungi using commercial enzymes. In Enzyme Microb. Technol., 1981, Vol. 3, October Andrews and Asenjo, Enzymatic lysis and disruption of microbial cells. In Tibtech, October 1987, Vol. 5

Hudson, H. J. in "Fungal Biology", eds. Willis, A. J. and Sleigh, M. A., 1986, Edward Arnold (Publishers), Ltd.).

Kofod et al., (1994), J. Biol. Chem., 261, 8407–8413 van den Hazel et al., (1992), Eur. J. Biochem., 207, 277–283

Becker and Guarente, (1991), Methods Enzymnol., 194, 182–187

Sherman, (1991), Methods Enzymol. 194, 3–21

Meissner et al., (1987), Proc. Natl. Acad. Sci. U.S.A., 84, 4171–4176

Devereux et al., (1984), Nucleic Acids Res., 12, 387–395

Laemmli et al. (1970), Nature, vol 227, p. 680–685

Christgau, Schierbeck et al., (1991), J. Biol. Chem, Vol 266, p. 21157–21164.

What is claimed is:

1. A DNA construct comprising a DNA sequence encoding an enzyme exhibiting endo-β-glucanase activity, wherein the DNA sequence is one of:
   (a) a DNA sequence comprising the sequence of SEQ ID NO:3,
   (b) a DNA sequence which encodes a polypeptide comprising the amino acid sequence of SEQ ID NO:4, or
   (c) a DNA sequence which hybridizes with the oligonucleotide probe comprising the DNA sequence of (a) under conditions of presoaking in 5×SSC, prehybridizing for 1 hr at ~50° C. in a solution of 5×SSC, 5×Denhardt's, 50 mM sodium phosphate, pH 6.8, and 50 µg denatured sonicated calf thymus DNA, followed by hybridization in tlle same solution for 18 h at ~50° C., followed by washing three times in 2×SSC, 0.2% SDS at 50° C. for 30 minutes.

2. The DNA construct of claim 1, wherein the endoglucanase activity is endo-1,3(4)-β-glucanase activity.

3. The DNA construct of claim 1, comprising a DNA sequence encoding an enzymne exhibiting endo-1,3(4)-β-glucannse activity, which DNA sequence comprises the DNA sequences shown in SEQ ID Nos. 1 or 2.

4. DNA construct of claim 1, wherein the DNA sequence encoding an enzymp- exhibiting endo-β-glucanase activity is obtainable from a mnicroorganism.

5. The DNA construct qf claim 4, wherein the DNA sequence is obtainable from a filamentous fungus or a yeast.

6. DNA construct of claim 5, wherein the DNA sequence is obtainable fom a strain of Trichoderma, Saecharomyces, Aspergillus, Penacillium, FusaInum, Hlumicola Acremonum, Borryrts, or Sclerolium.

7. DNA construct of claim 6, wherein the DNA sequence is obtainable from a strain of Trichoderma.

8. The DNA construct of claim 7, wherein the DNA sequence is obtainable from a strain of *Trichodernn hanianum*.

9. The DNA construct, of claim 8, wherein the DNA sequence is isolated from a DNA library of *Thchoderma harzianwn* CBS 243.71.

10. A DNA construct comprising a DNA sequence encoding an enzyme exhibiting endo-1,3(4)-β-glucanase activity, wherein the DNA sequence is obtainable from a strain of Acremonium sp. CBS 265.95 and comprises SEQ ID Nos. 5 and/or 6.

11. DNA construct of claim 10, wherein the DNA sequence is isolated from *Saccharomyces cerevisiae* NN049006.

12. A recombinant expression vector comprising a DNA construct according to claim 1.

13. A cell comprising the DNA construct of claim 1.

14. The cell of claim 13, which is a eukaryotic cell.

15. The cell of claim 14, wherein the eukaryotic cell is a fungal cell.

16. The cell of claim 15, wherein the fungal cell is yeast or filamentous fungi.

17. The cell of claim 16, wherein the cell belongs to a strain of Aspergillus.

18. The cell of claim 17, wherein the cell is a strain of *Aspergillus niger* or *Aspergillus oryzae*.

19. A method of producing an enzyme exhibiting endo-β-glucanase activity, the method comprising culturing the cell of claim 13 under conditions permitting the production of the enzyme, and recovering the enzyme from the culture.

20. A DNA construct comprising a DNA sequence encoding an enzyme exhibiting endo-β-glucanase activity, wherein the DNA sequence comprises the sequence of SEQ ID NO:3.

21. A DNA construct comprising a DNA sequence encoding an enzyme exhibiting endo-β-glucanase activity, wherein the DNA sequence encodes a polypeptide comprising the amino acid sequence of SEQ ID NO:4.

22. An isolated substantially pure culture of *Saccharonryces cerevislac* NN049006.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 369 base pairs
      (B) TYPE: nucleic acid
      (C) STRANDEDNESS: single
      (D) TOPOLOGY: linear (xi) SEQUENCE DESCRIPTION: SEQ ID NO:1:

| | | | | | |
|---|---|---|---|---|---|
|GTATATACAA|CATCAGTACA|TACTATATAC|CCTCCTTTTA|ACCCCTTTTT|GAAACATATA|60|
|CAAAATGTGG|TCTCCCAAGG|TTGCTGCTGC|CGTCCTCGCC|TTTGTTGGTG|CTACCAACGC|120|
|CTGGCAGCCC|CCGACCTACA|GCGGCTTCAA|CTTGGTCTGG|ACTGACACCT|TCGCTGGCAA|180|
|CGGTGGCACT|TCTCCTAACC|AGAACAACTG|AACATCATC|ACCGGAAACT|TGAACGTCAA|240|
|CGCCGAGCAG|GAGACCTACT|CCTCCAGCAC|CGCCAATGTT|CAGCTCAGTG|GTGGCAGCAC|300|
|CCTTCAGCTG|GTCCCCTGGA|GAGACAGCAG|CAAGGGAACA|GCACCTTTGG|TGGCTGGACC|360|
|TCGGCTGCT| | | | | |369|

(2) INFORMATION FOR SEQ ID NO:2:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (xi) SEQUENCE DESCRIPTION: SEQ ID NO:2:

| | | | | | |
|---|---|---|---|---|---|
|CCCTCACCTG|GTCCTCGACG|GCACCAACTA|CTTCCAGTCA|CTGGTTCTCG|CATTGGCAAC|60|
|CAGGGCGTCT|GGAACAACAT|TGCTCACAGC|CCCCTCTTCT|TCATTCTTAA|CGTTGCTGTC|120|
|GGTGGCAACT|GGCCTGGCAA|CCCCAACAGC|GCTACCCTCG|ATGGCTACGG|AAGCATGATG|180|
|GAGGTTGGCT|ACGTCGCTCA|GTACTCTACC|TAAGAACCTT|GCGCTCTTGA|GGTAGCTGTT|240|
|TGTGACATGC|GATACCACAG|TACATAAGCC|TGAGCTCGTC|TCAGGCTCAG|TGGCAAATTA|300|
|GGAGGATGAG|CATTTTCACT|TCCTCTTGTC|ACT| | |333|

(2) INFORMATION FOR SEQ ID NO:3:

(i) SEQUENCE CHARACTERISTICS:
        (A) LENGTH: 879 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| | | | | | |
|---|---|---|---|---|---|
|ATGTGGTCTC|CCAAGGTTGC|TGCTGCCGTC|CTCGCCTTTG|TTGGTGCTAC|CAACGCCTGG|60|
|CAGCCCCCGA|CCTACAGCGG|CTTCAACTTG|GTCTGGACTG|ACACCTTCGC|TGGCAACGGT|120|
|GGCACTTCTC|CTAACCAGAA|CAACTGGAAC|ATCATCACCG|GAAACTTGAA|CGTCAACGCC|180|
|GAGCAGGAGA|CCTACTCCTC|CAGCACCGCC|AATGTTCAGC|TCAGTGGTGG|CAGCACCCTT|240|
|CAGCTGGTCC|CCTGGAGAGA|CAGCAGCAAG|GGAACCAGCA|CCTTTGGTGG|CTGGACCTCC|300|
|GGTCGTCTTG|AGTCCAAGTA|CACATTCACT|CCCGCGGCCG|GCAAGGTCAC|CGTCTTGAA|360|
|GCCGCCATCC|GCTTCGGCAG|CAACGCTCAG|GCCAACAAGC|AGGGTATCTG|GCCTGCTTTC|420|
|TGGATGCTGG|GTGACTCCCT|CCGTCAACCG|GGCGGCAGCT|GGCCCAACTG|TGGTGAGATC|480|
|GACATCATGG|AGACTGTCGA|CGGCCAGGCT|ACCGGCCACG|GTACCCTTCA|CTGCGACGTC|540|
|TACCCCGGCG|GTATCTGCAA|CGAGGGTAAC|GGTATTGGAG|GCCCTGTCAA|CATCGCCAAC|600|
|GTCAACGACT|GGCACGCTTG|GCGTGTTGAG|ATCGACCGCA|CTCCCAGCAG|CTGGCAATCC|660|
|GAGACCCTCA|CCTGGTCCCT|CGACGGCACC|ATCTACTTCC|AGATCACTGG|CTCTCGCATT|720|
|GGCAACCAGG|GCGTCTGGAA|CAACATTGCT|CACAGCCCCC|TCTTCTTCAT|TCTTAACGTT|780|
|GCTGTCGGTG|GCAACTGGCC|TGGCAACCCC|AACAGCGCTA|CCCTCGATGG|CTACGGAAGC|840|

ATGATGGAGG TTGGCTACGT CGCTCAGTAC TCTACCTAA                                    879

(2) INFORMATION FOR SEQ ID NO:4:

(i) SEQUENCE CHARACTERISTICS:
        (A) LENGTH: 292 amino acids
        (B) TYPE: amino acid
        (C) STRANDEDNESS: single
        (D) TOPOLOGY: linear     (xi) SEQUENCE DESCRIPTION: SEQ ID NO:4:

```
Met Trp Ser Pro Lys Val Ala Ala Val Leu Ala Phe Val Gly Ala
 1               5                  10                  15

Thr Asn Ala Trp Gln Pro Pro Thr Tyr Ser Gly Phe Asn Leu Val Trp
             20                  25                  30

Asp Thr Phe Ala Gly Asn Gly Gly Thr Ser Pro Asn Gln Asn Asn
             35                  40                  45

Trp Asn Ile Ile Thr Gly Asn Leu Asn Val Asn Ala Glu Gln Glu Thr
 50                  55                  60

Tyr Ser Ser Ser Thr Ala Asn Val Gln Leu Ser Gly Gly Ser Thr Leu
 65                  70                  75                  80

Gln Leu Val Pro Trp Arg Asp Ser Ser Lys Gly Thr Ser Thr Phe Gly
                 85                  90                  95

Gly Trp Thr Ser Gly Arg Leu Glu Ser Lys Tyr Thr Phe Thr Pro Ala
                100                 105                 110

Ala Gly Lys Val Thr Arg Leu Glu Ala Ala Ile Arg Phe Gly Ser Asn
                115                 120                 125

Ala Gln Ala Asn Lys Gln Gly Ile Trp Pro Ala Phe Trp Met Leu Gly
130                 135                 140

Asp Ser Leu Arg Gln Pro Gly Gly Ser Trp Pro Asn Cys Gly Glu Ile
145                 150                 155                 160

Asp Ile Met Glu Thr Val Asp Gly Gln Ala Thr Gly His Gly Thr Leu
                165                 170                 175

His Cys Asp Val Tyr Pro Gly Gly Ile Cys Asn Glu Gly Asn Gly Ile
                180                 185                 190

Gly Gly Pro Val Asn Ile Ala Asn Val Asn Asp Trp His Ala Trp Arg
                195                 200                 205

Val Glu Ile Asp Arg Thr Pro Ser Ser Trp Gln Ser Glu Thr Leu Thr
210                 215                 220

Trp Ser Leu Asp Gly Thr Ile Tyr Phe Gln Ile Thr Gly Ser Arg Ile
225                 230                 235                 240

Gly Asn Gln Gly Val Trp Asn Asn Ile Ala His Ser Pro Leu Phe Phe
                245                 250                 255

Ile Leu Asn Val Ala Val Gly Gly Asn Trp Pro Gly Asn Pro Asn Ser
                260                 265                 270

Ala Thr Leu Asp Gly Tyr Gly Ser Met Met Glu Val Gly Tyr Val Ala
                275                 280                 285

Gln Tyr Ser Thr
        290
```

(2) INFORMATION FOR SEQ ID NO:5:

(i) SEQUENCE CHARACTERISTICS:
        (A) LENGTH: 208 base pairs
        (B) TYPE: nucleic acid
        (C) STRANDEDNESS: single
        (D) TOPOLOGY: linear -continued (xi) SEQUENCE DESCRIPTION: SEQ ID NO:5:

```
ATGCGCTTCG CTTCTTATCT TTCGTTGCTA CCCATTCTGG GAGCCAGCGT CTCAGCCTGG      60

GACGCACCGA GCTACGATGG GTACCGGCTT GTCTGGGCCG AGACCTTCGC AGGCCCCAGC     120

AACGGCCTTC CCAATGAGAA CAACTGGAAC ATCATCGACG GAAACATCGG CCGTCAACAA     180

CGAGCTCCAG ACGTACCGGC GGAACCCG                                        208
```

(2) INFORMATION FOR SEQ ID NO:6:

(i) SEQUENCE CHARACTERISTICS:
        (A) LENGTH: 171 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:6:

```
GGCGATCAAC TCAACGACCA GGGCGTCTGG GAGAGCTTGA CGGCCAAGCC TCTGTTCTTT      60

ATCCTGAATG TTGCGGTTGG CGGCAACTGG CCCGGCTATC CCAATGGCAA CACCCTTGGC     120

GGCTATGGCG CCATGATGGA AGTGGGCTAT GTTGCTCAGT ACTCCTCTTG A              171
```